United States Patent
Di Mino et al.

[11] Patent Number: 5,954,762
[45] Date of Patent: Sep. 21, 1999

[54] COMPUTER-CONTROLLED SERVO-MECHANISM FOR POSITIONING CORONA DISCHARGE BEAM APPLICATOR

[76] Inventors: Alfonso Di Mino, 15 Arcadia Rd.; Andre Di Mino, 159 Glen Rd., both of Woodcliff Lake, N.J. 07675

[21] Appl. No.: 08/929,023

[22] Filed: Sep. 15, 1997

Related U.S. Application Data

[63] Continuation-in-part of application No. 08/929,015, Sep. 15, 1997.

[51] Int. Cl.$^6$ ......................................................... A61N 1/02
[52] U.S. Cl. ........................... 607/149; 607/101; 607/109
[58] Field of Search ..................................... 607/145, 149, 607/150, 151, 154, 155, 72, 73, 96, 98, 99, 101, 109, 110, 112; 600/10, 13, 14

[56] References Cited

U.S. PATENT DOCUMENTS

| | | | |
|---|---|---|---|
| 3,617,684 | 11/1971 | Di Mino | 219/121.11 |
| 3,676,633 | 7/1972 | Di Mino | 219/69.13 |
| 4,667,677 | 5/1987 | Di Mino | 607/71 |
| 5,190,037 | 3/1993 | Di Mino et al. | 607/101 |
| 5,249,575 | 10/1993 | Di Mino et al. | 607/150 |
| 5,676,695 | 10/1997 | Di Mino et al. | 607/154 |

*Primary Examiner*—Jeffrey R. Jastrzab
*Attorney, Agent, or Firm*—Michale Ebert

[57] ABSTRACT

A computer-controlled, servo-mechanism associated with a system for treating a subject having a neuro-cerebral disorder characterized by internal lesions, the system including an applicator that projects a corona discharge beam toward an external site on the subject adjacent the lesions. The servo-mechanism is adapted to position the applicator to cause the beam projected therefrom to trace a pattern of movement on the site in accordance with a program entered into the computer controlling the mechanism, whereby all areas on the lesions are subjected by the beam to ion bombardment that acts to alleviate the disorder. To maintain the site steady during treatment, the subject is seated in and confined to a jig chair behind whose back rest is installed the servo-mechanism.

9 Claims, 3 Drawing Sheets

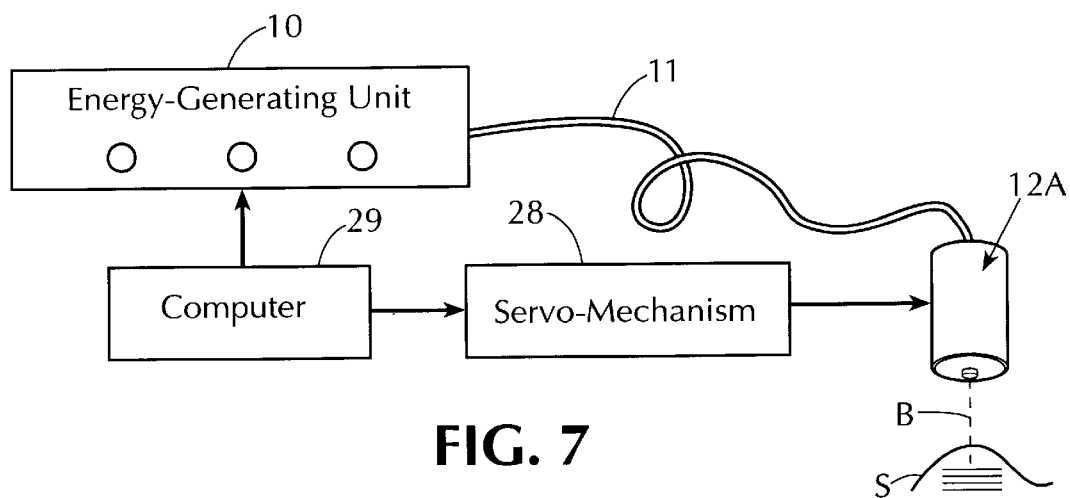
FIG. 7
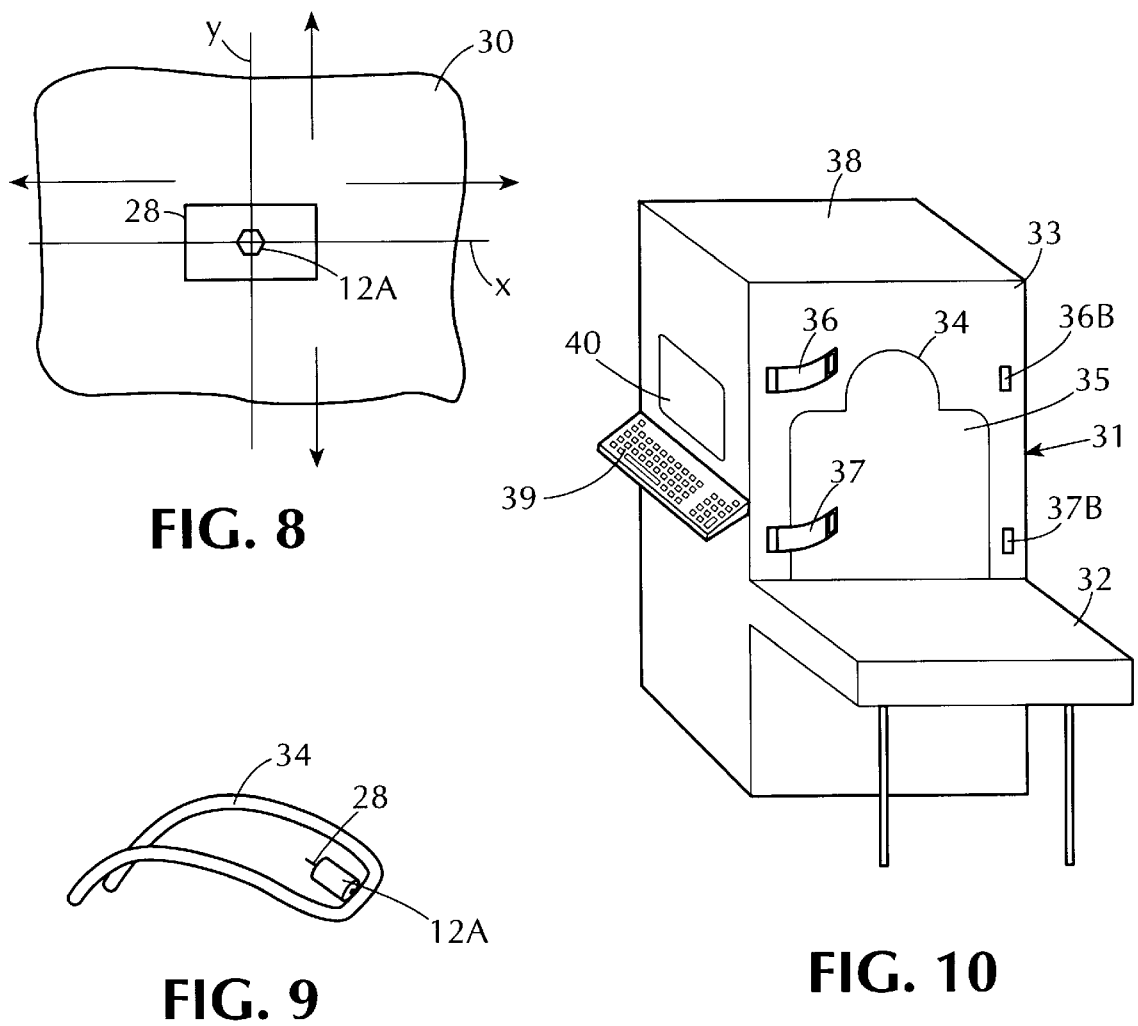
FIG. 8
FIG. 9
FIG. 10

COMPUTER-CONTROLLED SERVO-MECHANISM FOR POSITIONING CORONA DISCHARGE BEAM APPLICATOR

CROSS-REFERENCE TO RELATED APPLICATION

This application is a continuation-in-part of the DiMino application entitled "CORONA DISCHARGE TREATMENT OF NEURO-CEREBRAL DISORDERS" (Ser. No. 08/929,015, filed Sep. 15, 1997), whose entire disclosure is incorporated herein by reference.

BACKGROUND OF INVENTION

1. Field of Invention

This invention relates generally to the treatment of neuro-cerebral disorders characterized by lesions, such as multiple sclerosis, in which the lesions are subjected to a corona discharge beam projected from an applicator, and more particularly to a computer-controlled servo-mechanism adapted to position the applicator to cause the projected beams to trace a predetermined pattern on a site on the body of the subject be treated adjacent the lesions.

2. Status of Prior Art

The human brain is the supervisory center of the nervous system in which sensory nerve cells feed information to the brain from every region of the body, internal and external. The brain evaluates this incoming data and then sends directives through motor nerve cells to the muscles and glands to cause them to take appropriate actions. Thus if you touch a hot stove with a finger, the brain is informed of this fact by sensory nerve cells in the finger, and the brain then instructs motor nerve cells to pull the finger away from the stove.

Anatomically, the brain has three parts, the first being the hind brain which includes the cerebellum and the brain stem. The second part is the midbrain, and the third, the forebrain. The forebrain includes the cerebrum which is by far the largest sector of the brain and occupies the top most portion of the skull.

The cerebrum is split vertically into left and right hemispheres, the left hemisphere controlling the right side of the body and the right hemisphere the left side. The basal ganglia in each cerebrum hemisphere handles coordination as well as habitual but acquired skills.

The upper surface of the cerebrum is the cerebral cortex which incorporates the master controls of the body. It is in the cerebral cortex where incoming sensory data is analyzed and where motor impulses are originated to initiate, reinforce or inhibit muscle and gland activity.

It is well known that various neurological disorders are characterized by lesions in particular parts of the cerebrum (See: Principles of Neurology—Adams & Victor, 3rd Edition, McGraw—Hill—Chapter 21).

Thus the clinical manifestations of multiple sclerosis (MS) are determined by the location and extent of the foci of demyelination, the destruction of the myelin sheath of the nerve fibers. In the pathologic findings of ms, the brain and the spinal cord associated with the brain reveal numerous scattered lesions. These stand out from the surrounding white tissue in that the loss of myelin results in a pink-gray color.

The frontal lobes of the brain constitute about 30 percent of the cerebrum. Of the various effects of frontal lobe lesions, most is known about motor abnormalities caused thereby, such as spastic paralysis. Those abnormalities in motor functions which are referred to as cerebral palsy are characterized pathologically by cerebral lesions. These lesions can be identified by CT scans and ultrasound imaging. Cerebral lesions are also exhibited in Parkinson's disease which results in tremulous involuntary motion and lessened muscular power.

In a non-invasive therapeutic technique in accordance with the invention for treating neuro-cerebral disorders, the lesions which characterize these diseases are subjected to ionic bombardment by a pulsatory corona discharge beam projected from an applicator. Hence of prior art interest are applicants' prior patents which disclose corona discharge beam applicators for other purposes.

The Di Mino patents, U.S. Pat. Nos. 3,676,633 and 3,617,684 disclose a technique for changing the value of microelectronic resistors formed in a substrate. To bring about a decrease in resistance value, the surface of the resistor is subjected to a corona discharge beam. This beam is produced by radio-frequency energy which is amplitude-modulated by an audio frequency signal to generate bursts of energy which are applied to a discharge electrode from which the corona discharge beam is projected.

A luminous corona discharge is brought about as a result of the ionization of air surrounding an electrode. This phenomenon occurs when the potential gradient exceeds a certain value, but is not sufficient to cause breakdown of the air which results in sparking. When the luminous corona discharge extends from a point on the electrode to a surface spaced from this point, then the discharge is in the form of a linear beam rather than a halo.

Of greater prior art interest are the patents to Di Mino U.S. Pat. Nos. 4,667,677 and 5,249,575 which disclose a corona discharge technique for therapeutically treating human and animal subjects. In this technique, a corona-discharge beam is projected from an electrode toward an external site on the body being treated overlying a problem region. This beam serves to relieve pain and to gain other salutary effects, such as to alleviate an arthritic condition.

The system disclosed in Di Mino patent U.S. Pat. No. 5,249,575 includes an energy-generating unit in which a radio-frequency carrier is overmodulated by an audio-frequency signal to produce periodic bursts of radio-frequency energy whose repetition rate corresponds to the audio frequency of the signal. The output of this unit is fed by a flexible coaxial cable to a tank circuit tuned to the carrier frequency and housed within the barrel of a portable applicator gun on whose grip is mounted a trigger switch operatively connected to the unit.

Supported within the barrel and coupled to the tank circuit is a discharge electrode whose tip is adjacent the mouth of the barrel. When an operator holding the gun actuates the trigger switch, the unit is turned on and a corona discharge beam is then projected from the electrode tip, the operator positioning the gun to direct the beam toward the skin surface to be treated.

Though a system of the type disclosed in the Di Mino '575 patent is useful in relieving pain or in realizing other therapeutic effects, the corona discharge beam produced by this system is not effective to a significant degree in the treatment of neuro-cerebral disorders.

In above-identified copending DiMino application there is disclosed a system for treating neuro-cerebral disorders, such as multiple sclerosis, that are characterized by internal lesions. The system includes an applicator from which is projected a pulsatory corona discharge beam which is directed toward an external site on the body of the subject being treated adjacent the internal lesions. The beam is scanned over the site to bombard the lesions with ions for a period sufficient to alleviate the disorder.

To carry out this treatment the applicator which has a gun-like format is hand-held by an operator and manipulated to project the corona discharge beam toward a site on the body of the subject being treated that is adjacent the lesions. This site may for example be on the skull of the subject overlying the two cerebrum hemispheres in which the lesions are located. In other cases, the site may be in the region of the spine adjacent the brain, the selected site depending on the location of the lesions in the particular disorder being treated.

In order to subject all areas of the lesions to the corona discharge beam, the operator must manipulate the applicator so that the beam scans the site to traverse all areas of the adjacent lesions, and to do so for a period of treatment which usually lasts several minutes.

This manual procedure for manipulating the corona beam applicator is not only difficult to carry out, but it is also somewhat deficient in regard to proper treatment of the subject suffering from a neuro-cerebral disorder. Thus it is desirable for proper treatment that the operator hold the applicator in the course of treatment a short fixed distance from the selected site on the body of the subject, so that the corona discharge beam always bridges this distance. It is not only hard for an operator to maintain this distance for the several minutes of treatment, but it is even more difficult for the operator to be sure that all areas of the site are scanned with the beam for a sufficient period of time to effect proper treatment.

Moreover, proper treatment dictates that the site on the subject exposed to the corona discharge beam remain steady during the several minutes of treatment. Thus if the site of treatment on the subject is a section of his skull below which are the two hemispheres of the cerebrum, and the subject is seated on a chair, he may find it quite difficult to hold his head steady in the course of several minutes of treatment.

SUMMARY OF INVENTION

In view of the foregoing, the main object of this invention is to provide a computer-controlled, servo-mechanism adapted to position an applicator from which is projected a corona discharge beam, to cause the projected beams to trace a predetermined pattern of movement on a site on the body of the subject being treated for a neuro-cerebral disorder characterized by lesions which are adjacent the site.

More particularly an object of this invention is to provide a computer-controlled, servo-mechanism, of the above type in which this pattern of movement traced by the corona discharge beam is in accordance with a program entered into this computer which is appropriate to the subject being treated.

Among the significant features of the invention are the following:

A. the computer-controlled, servo-mechanism makes it possible to achieve repeatable and consistent treatment from patient-to-patient; and B. the program entered into the computer serves not only to dictate the pattern of beam movement, but also to control the energy-generating unit coupled to the applicator producing the corona discharge beam to govern the period and intensity of treatment.

Also an object of the invention is to provide a jig chair in which the subject being treated is seated and confined, to maintain the site exposed to the corona discharge beam in a steady state.

Briefly stated, these objects are attained by a computer-controlled, servo-mechanism associated with a system for treating a subject having a neuro-cerebral disorder characterized by internal lesions, the system including an applicator that projects a corona discharge beam toward an external site on the subject adjacent the lesions.

The servo-mechanism is adapted to position the applicator to cause the beam projected therefrom to trace a pattern of movement on the site in accordance with a program entered into the computer controlling the mechanism, whereby all areas on the lesions are subjected by the beam to ion bombardment that acts to alleviate the disorder. To maintain the site steady during treatment, the subject is seated in and confined to a jig chair behind whose back rest is installed the servo-mechanism.

BRIEF DESCRIPTION OF DRAWING

For a better understanding of the invention reference is made to the attached drawing wherein:

FIG. 7 is a block diagram of a computer controlled, servo-mechanism in accordance with the invention adapted to position a corona discharge beam applicator;

FIG. 8 illustrates the changing position of the applicator in rectangular coordinates;

FIG. 9 shows a guide for the applicator; and

FIG. 10 shows a jig chair for the subject being treated.

DETAILED DESCRIPTION OF INVENTION

The Basic System

Figure 1:
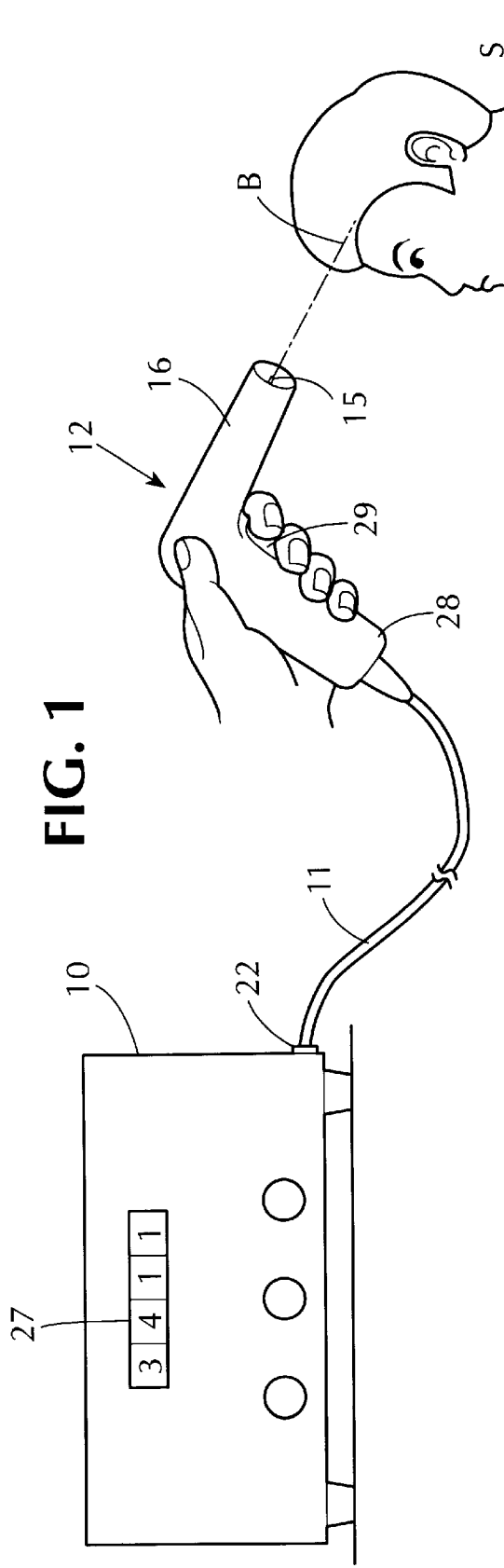
FIG. 1 illustrates the basic components of a corona-discharge beam system in accordance with the invention for treating neuro-cerebral disorders.

Referring now to FIG. 1 showing a system in accordance with the invention, included in this system is an energy-generating unit 10 in which a radio frequency carrier is modulated by an audio frequency signal. This signal is chopped into pulses which cyclically, in the course of each minute, have a progressively stepped repetition rate.

Modulating of the R-F carrier by the chopped audio signal results in corresponding bursts of radio-frequency energy which are applied to a discharge electrode from which is projected a pulsatory corona-discharge beam.

The bursts of radio-frequency energy yielded by unit 10 are fed by a flexible cable 11 to a hand-held applicator gun 12 within whose barrel 16 is mounted a discharge electrode 15 from which the corona-discharge beam B is projected.

Figure 2:
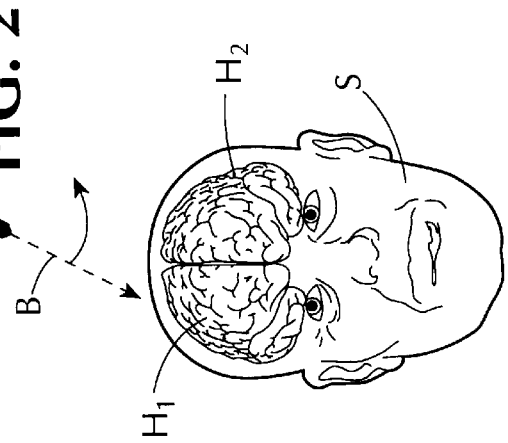
FIG. 2 shows the direction of the corona-discharge beam with respect to the cerebrum of the brain of a subject being treated.

Beam B is directed toward an external sites on the body of a subject suffering from a neuro-cerebral disorder, such as multiple sclerosis, characterized by lesions, site S on which beam B impinges, being adjacent these lesions. Thus, as shown in FIG. 2, beam B may be applied to a site on the skull of subject below which are the left and right hemispheres $H_1$ and $H_2$ of the cerebrum containing the lesions.

Or the corona-discharge beam, when treating other neuro-cerebral disorders, may be projected towards a site overlying the lower ganglia, or one adjacent the spinal column.

In practice, by means of a CT scan, an ultrasound instrument, or other imaging apparatus, one may locate the lesions characterizing the neuro-cerebral disorder to be treated. In this way one can concentrate the corona-discharge beam 12 at a site on the subject that is adjacent these lesions. And the beam B is manipulated so as to scan all areas of the site to bombard the lesions with ions for a period sufficient to reduce the visible symptoms of the disorder, and thereby alleviate the disorder.

Because the corona-discharge beam is pencil-like and therefore impinges on a site in which the zone of engagement is small, in order to irradiate a site having a relatively large area, the beam is scanned over this area so that the entire area is subjected to treatment.

A corona-discharge is a highly active glow region surrounding a discharge electrode. When the electrode is a pointed wire or rod as in the present case, this glow region extends a short distance beyond this point. Assuming the wire is negatively charged, the free electrons in the air in the region of the intense electric field surrounding the wire, gains energy in this field to produce positive ions and other electrons by collision. In turn, these new electrons are accelerated and produce further ionization. This cumulative process results in an electronic avalanche in which the positive ions are accelerated toward and bombard the charged wire. As a consequence of such ionic bombardment, secondary electrons are ejected from the tip of the electrode which act to sustain the corona discharge.

When the voltage applied to the discharge electrode is elevated to a level exceeding the point at which a stable corona discharge is maintained, the air dielectric then completely breaks down to cause a spark discharge. In order therefore to produce a corona discharge, the peak voltage on the discharge electrode must be relatively high but below the level resulting in a spark discharge.

The continuous application of radio-frequency energy of relatively low power to an electrode will not result in a corona discharge. But because in energy-generating unit 10, radio-frequency energy is produced in short bursts which shock-excite a tank coupled to a discharge electrode, the resultant energy surges have a peak amplitude sufficient to produce a sustained corona discharge beam.

The Energy Generating Unit

Figure 3:
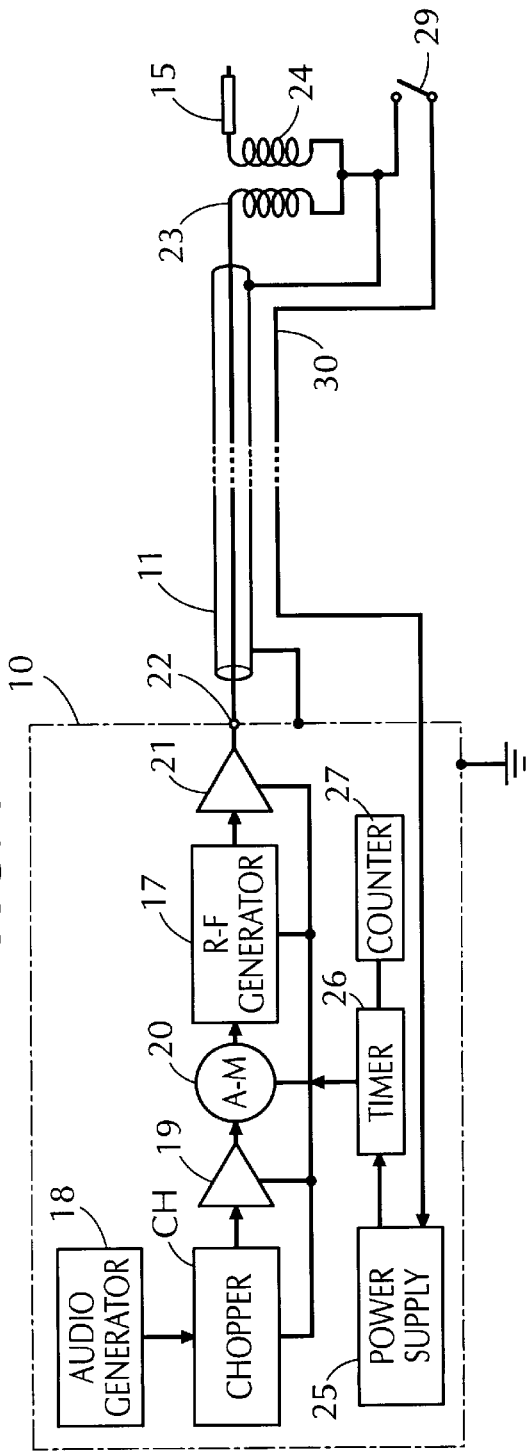
FIG. 3 is a block diagram showing the various stages of the energy-generating unit included in the system and the applicator gun connected to the output of the unit.

Referring now to FIG. 3, energy generating unit 10 includes a radio-frequency oscillator 17 producing an R-F carrier lying in the low frequency R-F range of 200,000 to 450,000 Hz. A preferred carrier frequency is 430,000 Hz. In practice, this oscillator may be frequency-controlled by a piezoelectric crystal, the R-F carrier also being stabilized as to amplitude.

Also included in unit 10 is an audio-frequency signal generator 18 operating in the audio-frequency range of 300 to 1000 Hz to produce a sonic signal. A preferred audio frequency is 420 Hz. This audio signal which is chopped into pulses by a chopper CH in a manner to be later described, is amplified in amplifier 19 and applied to an amplitude modulator 20. Modulator 20 is so connected to radio-frequency oscillator 17 as to effect amplitude modulation of the R-F carrier.

In amplitude-modulation, the amplitude of the radio-frequency carrier is varied in accordance with the audio signal, the resultant modulated wave containing side bands that are the sum and difference of the carrier and audio signal frequencies. If the modulation index "M" is zero, no signal information is conveyed to the carrier. When, however, M=1 (100% modulation), then in the case of a sinusoidal carrier wave, the envelope of the carrier varies from zero to twice the value of its unmodulated amplitude. But if "M" exceeds unity, the carrier is then overmodulated, as a consequence of which the carrier is periodically interrupted at a repetition rate in accordance with the audio-frequency signal.

The radio frequency carrier produced by R-F oscillator 17 is overmodulated by an audio signal that is chopped into pulses by chopper CH, this resulting in bursts of radio-frequency energy which correspond to the chopped audio pulses. The bursts of energy from R-F oscillator 17 are applied through an output amplifier 21 to the output jack 22 of the energy-generator unit.

Plugged into output jack 22 of the energy generating unit 10 is one end of coaxial cable 11 which connects the output of the unit to the tank coil 23 of a tank circuit. The tank circuit is housed within barrel 16 of applicator gun 12, the tank coil being tuned to the carrier frequency of the unit. Tank coil 23 is inductively coupled to an output coil 24 to which is connected the discharge electrode 15. It is to be noted that the outer shielding conductor of coaxial cable 11 is grounded, the inner conductor connecting one end of the tank coil 23 to output jack 22, the other end of the tank coil and the corresponding end of the output coil being connected to the grounded conductor. Because of this arrangement, there is no radiation from the coaxial cable.

Because tank coil 23 is shock excited by the bursts of the radio-frequency energy, the resultant damped wave surges in coil 23 have a high peak amplitude, and this causes the desired corona discharge to produce a beam which is both visible and audible. The reason it is visible is that the corona beam in the region adjacent the electrode tip produces a blue glow, and the reason it is audible is that the bursts of energy are at a sonic rate and can therefore be heard. In practice, the power output of the system may be in the order of 5 to 15 watts.

Unit 10 is provided with a direct-current power supply 25 whose output is applied to the various stages of the unit through a cycle timer switch 26 so that the unit is activated only when the cycle timer switch is "on." Thus the timer switch may be set to cyclically activate the unit for a predetermined time period, say for five minutes, during which a pulsatory corona discharge beam is produced to treat a neuro-cerebral disorder, this period being followed by a shorter relaxation interval, say two minutes, during which the timer switch is turned off. The cyclical operation of the unit prevents subjecting the subject to an overdose of ions and also prevents overheating of the unit itself should the unit be kept on continuously for a prolonged period.

The cycle timer also makes it possible to meter the dosage applied to the subject; this being done by a resettable digital counter 27 coupled to the timer.

Gun 12 is provided with a grip 28 having a trigger switch 29 mounted thereon. This switch, one contact of which is grounded, is connected by a line 30 to power supply 25. In this way, the unit 10 is only turned on when an operator holding gun 12 in his hand actuates the trigger switch. In practice, the trigger switch may be arranged to actuate a relay having a time delay characteristic, so that once the trigger is momentarily pulled, the unit is turned on for, say, a 15-second interval, and does not release until this interval is completed.

The applicator gun may be shaped like a typical hair blow dryer, and it is even lighter than such a dryer, for all it contains is the tank circuit and the discharge electrode. Because the operator is free to manipulate the gun which is connected to unit 10 by a long cable (say 6 feet in length), he is able to treat any site on the subject.

The Chopper Action

In the corona-discharge beam system disclosed in the above-identified DiMino prior patents in which the beam when applied to a human or animal subject serves to relieve pain or an arthritic condition, the corona beam is produced by applying to a discharge electrode periodic bursts of R-F energy. These bursts are produced by modulating an R-F carrier with a signal having an audio frequency. Thus if the R-F carrier has a frequency of 400,000 Hz, and the audio signal has a frequency of 300 Hz then bursts of R-F energy having a frequency of 400,000 Hz occur at a rate of 300 bursts per second.

In a technique in accordance with the invention for treating neuro-cerebral disorders, the corona-discharge beam serves to inject ions into the lesions which characterize the disorder being treated. In order to achieve effective penetration of these ions into the lesions, it is necessary that the ions bombarding the lesions cyclically increase in volume and therefore in intensity as to flow in a wave-like manner into the lesions. This wave-like flow of ions acts to modify the cellular structure of the lesions rather than to destroy their structure.

Chopper CH divides the audio signal from audio generator 18 applied to amplitude modulator 20 into audio pulses in accordance with a predetermined cyclical pulse pattern. In practice, chopper CH may take the form of a power transistor pulse-activated by a pulse generator controlled by a microprocessor programmed to produce the desired cyclical pulse pattern.

A preferred form of pulse pattern is one in which in the course of fixed period having a one minute duration during which the audio signal is applied to the power transistor, the transistor is activated to chop the audio signal into audio pulses in accordance with the pattern. The nature of the pattern is such that in the course of each cycle which lasts for a one minute period, the resultant audio pulses have a progressively stepped-up repetition rate.

It is these audio pulses which modulate the R-F carrier yielded by oscillator 18 and result in corresponding bursts of R-F energy that are applied to discharge electrode 15 to produce a pulsatory corona discharge beam that is effective in treating neuro-cerebral disorders.

Figure 5:
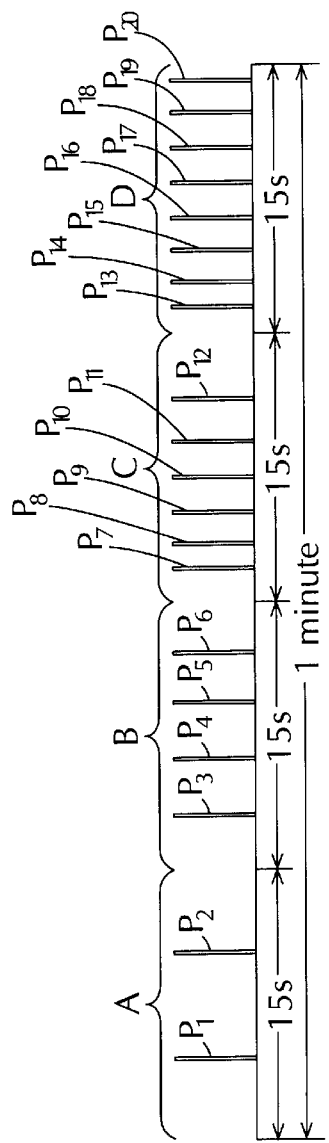
FIG. 5 shows the pulses produced by chopping the audio signal which modulates the radio frequency carrier produced in the energy-generating unit.

FIG. 5 illustrates the audio pulse pattern cyclically produced by chopper CH during each one minute period of the audio signal, in which the period is divided into four 15 seconds segments A, B, C and D. The chopper action is such that in the first 15 seconds segment A, there are produced two audio pulses $P_1$ and $P_2$ per second. Hence in the course of the 15 seconds segment A, chopper CH produces 30 pulses.

In the second 15 seconds segment B, chopper CH produces four audio pulses $P_3$, $P_4$, $P_5$ and $P_6$, per second. Hence in the course of this 15 seconds segment, chopper CH produces 60 pulses. In the third segment D, chopper CH produces six audio pulses $P_7$ to $P_{12}$, per second, thereby yielding 60 pulses in the course of this 15 seconds segment. And is the last segment C, chopper CH produces eight audio pulses $P_{13}$ to $P_{20}$, per second, thereby yielding 90 pulses in the course of this 15 seconds segment.

Figure 6:
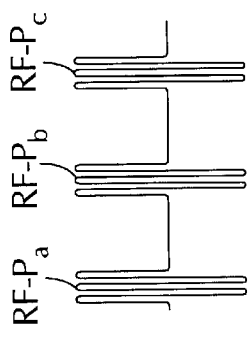
FIG. 6 illustrates the pulsatory radio-frequency carrier applied to the discharge electrode.
Figure 4:
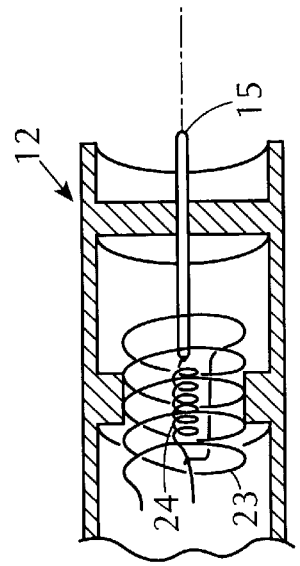
FIG. 4 is a section taken through the barrel of the gun.

Therefore during each cyclical period of operation, the bursts of R-F energy produced by the energy-generating unit 10 and applied to discharge electrode 15 correspond to the chopped audio pulses $P_1$ to $P_{20}$, and have the same progressively stepped up pattern. Thus, as shown in FIG. 6 the first three R-F bursts are RF-$P_a$, RF-$P_b$ and RF-$P_c$, these being the first three pulses in the first 15 seconds segment A in which 30 pulses are produced.

The R-F energy bursts in the course of each minute period have a progressively stepped up repetition rate, for in the first 15 seconds segment, the repetition rate is two pulses per second, in the second 15 seconds segment, it is four pulses per second, in the third segment, it is six pulses per second, and in the fourth segment it is eight pulses per second. The same pulse pattern is repeated in the course of the succeeding minute periods of operation.

Hence in the course of each minute period of operation the volume and therefore the intensity of ions produced by the corona-discharge beam bombarding the lesions increases in progressive steps from a low to a high intensity. And since the operation is cyclical, the flow of ions toward the lesions assumes a wave-like form which invades the cellular structure of the lesions to bring about a remedial action which ameliorates the neuro-cerebral disorder being treated.

We have found that patients having neuro-cerebral disorders characterized by lesions who are treated by a technique in accordance with the invention exhibit a significant reduction in the symptoms indicative of this disorder. Thus in treating patients suffering from Parkinson's disease, the tremors resulting from this disease were measurably reduced.

Computer-Controlled, Servo-Mechanism

Referring now to FIG. 7, shown therein is a servo-mechanism 28 whose purpose is to position an applicator 12A from which a corona discharge beam is projected toward a site S on the subject to be treated for a neuro-cerebral disorder. Servo-mechanism 28 is controlled by a digital computer 29 in which is entered a program that instructs the servo-mechanism how to position the applicator.

Applicator 12 shown in FIG. 1 is gun-like to facilitate it being grasped by the hand of an operator who manually manipulates the applicator to direct the corona discharge beam projected therefrom toward a site to be irradiated by the beam. But applicator 12A need not be gun-like, for it is not manipulated by hand but by servo-mechanism 28 which automatically changes the position of the applicator to cause beam B projected therefrom to trace a pattern of movement on the site S on the subject being treated in accordance with a program entered into the computer.

Because this pattern conforms to the program entered into the computer and the program is tailored to the patient being treated, repeatable and consistent treatment is made possible from patient-to-patient.

In FIG. 7, as in FIG. 1, the corona discharge beam is produced by a system including an energy-generating unit 10. Unit 10 generates bursts of R-F energy which are applied through cable 11 to the tank circuit in the applicator to shock excite this circuit whose output is applied to a discharge electrode from which the beam is projected, as previously disclosed.

The treatment period during which energy-generating unit remains operative, say three or five minutes, and the power output of the unit, say 5 or 10 watts, depends on the patient to be treated. Thus one patient having a particular neuro-cerebral disorder may require a short period of low power treatment, while another patent may have a disorder for which a longer and more intense treatment is appropriate.

Computer 29 in which is entered the program governing the pattern of beam movement appropriate for treating a given patient also has entered therein a program by which the computer governs the operation energy-generating unit 10 so that the period during which this unit is operative and its output power are suitable for the patient.

A servo-mechanism is a form of feedback control device to effect adapted automatic control of a mechanical apparatus, such as a steering mechanism. Hence by means of a servo-mechanism, a steering mechanism can be made to steer in accordance with a predetermined program.

A complete electromechanical set of one or more servo-mechanisms including all of the associated circuits and hardware adapted to carry out a specific task is called a servo system. Servo-mechanism 28 in combination with computer 29 which instructs the servo mechanism to change the position of applicator 12A in accordance with a program entered in the computer constitutes a servo system.

As pointed out previously, in order to effect proper treatment of a neuro-cerebral disorder, the corona-discharge beam projected from applicator 12A must trace a pattern of movement on the site adjacent the lesions so as to traverse all areas of the lesions to irradiate these areas with ions from the beam.

The pattern of movement that is appropriate depends on the nature and placement of the site, by way of example we shall in connection with FIG. 8 assume that site 30 has a generally rectangular area, and that servo-mechanism 28 therefore functions to shift applicator 12A across site 30, line by line along an X axis. Each scan along the X axis is shifted incrementally along a Y axis at right angles to the X axis. Hence when applicator 12A is positioned to scan the entire field of site 30, in the manner of a TV raster, all areas of the lesions adjacent this field are subjected to the corona discharge beam and are treated thereby.

When the corona discharge beam is to be projected toward a site on the skull of a subject to treat lesions underlying the site, then as shown in FIG. 9, applicator 12A positioned by servo-mechanism 28 operates within a track defined by an arcuate saddle 31 that is placed over the skull site to limit movement of the applicator to the track.

The Jig Chair

In a servo-mechanism which changes the position of a corona beam applicator with respect to a site on a subject to be treated, it is important that the site be maintained in a steady state in the course of treatment. In this way the pattern of beam movement lies within the boundaries of the site and therefore irradiates the lesions underlying the site and does not go beyond these boundaries.

To maintain the site steady, there is provided a jig chair 31 as shown in FIG. 10. Chair 31 has a seat 32 on which the patient to be treated sits with his back placed against a back rest panel 33. Combined with this chair is the servo system shown in FIG. 7 in which a corona discharge beam B is projected from applicator 12A which is positioned by computer-controlled servo-mechanism 28 to cause the beam to trace a pattern of movement on the site S of the subject being treated for a neuro-cerebral disorder. The function of the jig chair therefore is to maintain the site steady in the course of treatment.

Back rest panel 33 of the chair is provided with a shaped cut out 34 having a rectangular main section corresponding to the torso of the seated patient whose back rest abuts the back panel, and a head section above the rectangular section corresponding to the head of the patient. Cut out 34 is covered by a sheet 35 of, translucent film material or a polyester or fine nylon fabric against which is pressed the skin of the patient seated in the chair.

To confine the seated patient to the chair, two straps 36 and 37 are provided. Strap 36 extends from a mount on one side of back panel 33 over the head of the subject to a holding buckle 30B on the other side, this strap pressing the rear of the head against the back rest panel. Strap 37 extends from a mount on one side of back rest panel 33 over the torso of the patient to a holding buckle 37B on the other side to press the rear of the torso against the back rest panel.

In this way the patient is effectively immobilized in the course of treatment and the site to which is applied the corona discharge beam is prevented from shifting.

Servo mechanism 28 and applicator 12A positioned thereby are housed in a cabinet 38 behind back rest panel 33 so that the beam from the applicator is directed to a site on the patient whose skin is pressed against the thin sheet 35.

The computer controlling the servo-mechanism is also housed in cabinet 38. The keyboard 39 for the computer by which instructions are entered is mounted on a side of cabinet 38, video screen 40 of the computer terminal being mounted above the keyboard.

While there has been shown and described a computer-controlled, servo-mechanism for positioning corona discharge beam applicator in accordance with the invention, it will be appreciated that many changes and modifications may be made therein without, however, departing from the essential spirit thereof.

We claim:

1. In combination with a therapeutic system adapted to treat a subject having a neuro-cerebral disorder characterized by internal lesions by means of an applicator projecting a corona discharge beam toward an external site on the body of the subject overlying the lesions, a control system for positioning the applicator to cause the beam projected therefrom to trace a pattern of movement on the site whereby all areas of the lesions underlying the site are treated by the beam; said control system comprising:

A. a servo-mechanism coupled to said applicator to position the applicator; and

B. a computer controlling the applicator in accordance with a program entered therein to cause the beam projected from the applicator to trace said pattern.

2. A combination as set forth in claim 1, in which the therapeutic system includes an energy-generating unit which applies pulses of radio-frequency energy to a discharge electrode in said applicator from which the beam is projected.

3. A combination as set forth in claim 2, in which the period during which the energy-generating unit is operative to effect treatment and the amount of power produced by the unit are controllable, so that the treatment can be made appropriate to the subject being treated.

4. A combination as set forth in claim 3, in which the computer is coupled to the energy-generating unit and is programmed to effect control of the treatment period and the amount of power.

5. A combination as set forth in claim 1, further including means coupled to the applicator to maintain the site steady in the course of treatment.

6. A combination as set forth in claim 5, in which said means are constituted by a jig chair in which the subject is seated and confined, the chair having a back rest panel against which the rear of the seated and confined subject is pressed.

7. A combination as set forth in claim 6, in which the chair is provided with straps to confine the subject to the chair.

8. A combination as set forth in claim 6, which includes a cabinet behind the back rest panel in which is housed said servo-mechanism and the applicator.

9. A combination as set forth in claim 8, in which the computer controlling the servo-mechanism is housed in the cabinet.

* * * * *